United States Patent
Wong

(10) Patent No.: US 10,261,068 B2
(45) Date of Patent: Apr. 16, 2019

(54) PERSEVERE-II: REDEFINING THE PEDIATRIC SEPSIS BIOMARKER RISK MODEL WITH SEPTIC SHOCK PHENOTYPE

(71) Applicant: CHILDREN'S HOSPITAL MEDICAL CENTER, Cincinnati, OH (US)

(72) Inventor: Hector R. Wong, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 0 days.

(21) Appl. No.: 15/171,418

(22) Filed: Jun. 2, 2016

(65) Prior Publication Data

US 2016/0356762 A1     Dec. 8, 2016

Related U.S. Application Data

(60) Provisional application No. 62/170,957, filed on Jun. 4, 2015.

(51) Int. Cl.
| | | |
|---|---|---|
| G01N 33/49 | (2006.01) | |
| C12Q 1/06 | (2006.01) | |
| A61M 1/36 | (2006.01) | |
| A61M 1/34 | (2006.01) | |
| A61M 1/16 | (2006.01) | |
| G01N 33/50 | (2006.01) | |

(52) U.S. Cl.
CPC ........... *G01N 33/49* (2013.01); *A61M 1/1698* (2013.01); *A61M 1/3496* (2013.01); *A61M 1/3666* (2013.01); *C12Q 1/06* (2013.01); *G01N 33/5094* (2013.01); *G01N 2333/47* (2013.01); *G01N 2333/523* (2013.01); *G01N 2333/5421* (2013.01); *G01N 2333/96436* (2013.01); *G01N 2333/96494* (2013.01); *G01N 2800/26* (2013.01); *G01N 2800/56* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 7,645,573 B2 | 1/2010 | Ivey et al. | |
| 8,969,017 B2 * | 3/2015 | Mickiewicz | G01R 33/465 424/520 |
| 9,238,841 B2 * | 1/2016 | Wong | C12Q 1/6883 |
| 9,267,175 B2 * | 2/2016 | Wong | C12Q 1/6883 |
| 2003/0194752 A1 | 10/2003 | Anderson et al. | |
| 2004/0121343 A1 | 6/2004 | Buechler et al. | |
| 2010/0279878 A1 | 11/2010 | Wong | |
| 2011/0059858 A1 | 3/2011 | Kas et al. | |
| 2011/0312521 A1 | 12/2011 | Chaussabel | |
| 2015/0005189 A1 | 1/2015 | Wong et al. | |
| 2015/0018238 A1 | 1/2015 | Wong et al. | |

FOREIGN PATENT DOCUMENTS

| | | |
|---|---|---|
| EP | 2085486 A1 | 8/2009 |
| WO | WO-2006/113833 A2 | 10/2006 |
| WO | WO-2006/113833 A3 | 10/2006 |
| WO | WO-2008/143890 A2 | 11/2008 |
| WO | WO-2008/143890 A3 | 11/2008 |
| WO | WO-2009/095786 A2 | 8/2009 |
| WO | WO-2009/095786 A3 | 8/2009 |
| WO | WO-2009/095840 A1 | 8/2009 |
| WO | WO-2012/106396 A2 | 8/2012 |
| WO | WO-2012/106396 A9 | 8/2012 |
| WO | WO-2013/119869 A1 | 8/2013 |
| WO | WO-2013/119871 A1 | 8/2013 |

OTHER PUBLICATIONS

Dellinger et al., Intensive Care Med., 39:165-228 (2013).*
Venkata et al., J. Intensive Care, 1(9):1-10 (2013).*
Boechat et al., Rev. Bras. Ter. Intensiva., 24(1):35-42 (2012).*
Spies et al., Lancet, 361:989-994 (2003).*
Wong et al., Critical Care, 16(R174):1-9 (2012).*
Wong et al., Plos One, 9(1-e86242) (2014).*
Chen et al., Int. J. Clin. Exp. Med., 9(2):4029-4034 (2016).*
Guclu et al. Af. Health Sci., 13(2):333-338 (2013).*
Nguyen et al., Crit. Care, 10(6):1-8 (2006).*
Sharron et al., Plos One, PLoS One 7(7):e41549 (2012).*
Alder et al., "The pediatric sepsis biomarker risk model: potential implications for sepsis therapy and biology," Expet Rev. *Anti Infect. Ther.*, 2014, pp. 809-816, vol. 12(7).
Allen, T.C. et al. (Mar. 2007). "Anti-interleukin 8 autoantibody:interleukin 8 immune complexes visualized by laser confocal microscopy in injured lung," *Arch Pathol Lab Med* 131(3):452-456.
Allison et al., "Microarray data analysis: from disarray to consolidation and consensus," *Nat. Rev. Genet.*, Jan. 2006, pp. 55-65, vol. 7(1) [abstract only].
Aneja, R.K. et al. (Oct. 2011). "Differences between adult and pediatric septic shock," *Minerva Anestesiol* 77(10):986-992.
Brierley, J. et al. (2009). "Clinical Practice Parameters for Hemodynamic Support of Pediatric and Neonatal Septic Shock: 2007 Update from the American College of Critical Care," *Crit Care Med* 37(2):666-688.
Che et al., "Decision tree and ensemble learning algorithms with their applications in bioinformatics," *Adv. Exp. Med. Biol.*, 2011, 191-199, vol. 696.
Cohen, J. et al. (May 2015, e-published Apr. 19, 2015). "Sepsis: a roadmap for future research," *Lancet Infect Dis* 15(5):581-614.
Cornell et al., "Mechanisms and regulation of the gene-expression response to sepsis," *Pediatrics.*, Jun. 2010, pp. 1248-1258, vol. 125(6).

(Continued)

*Primary Examiner* — Thomas J. Visone
(74) *Attorney, Agent, or Firm* — Muriel Liberto, Esq.; Mintz Levin Cohn Ferris Glovsky and Popeo, P.C.

(57) ABSTRACT

The methods disclosed herein relate to an improved tool incorporating platelet count into a multi-biomarker based outcome risk stratification model for evaluating mortality risk in pediatric patients having sepsis. The methods described here are useful for treating sepsis, for point of care clinical decision support, for stratifying septic shock patients based on baseline mortality risk, and for clinical trial design, among other uses.

6 Claims, 3 Drawing Sheets

(56) References Cited

OTHER PUBLICATIONS

Cvijanovich et al., "Validating the genomic signature of pediatric septic shock," *Physiol. Genomics.*, Jun. 12, 2008, pp. 127-134, vol. 34(1).
Dellinger et al., "Surviving Sepsis Campaign: international guidelines for management of severe sepsis and septic shock: 2008," A2, 2 pages.
Dellinger et al., "Surviving sepsis campaign: international guidelines for management of severe sepsis and septic shock: 2012," *Crit. Care Med.*, Feb. 2013, pp. 580-637, vol. 41(2).
Freishtat et al., "Sepsis Alters the Megakaryocyte-Platelet Transcriptional Axis Resulting in Granzyme B-mediated Lymphotoxicity," *Am. J. Respir. Crit. Care Med.*, 2009, pp. 467-473, vol. 179.
Goldstein et al. "International Pediatric Sepsis Consensus Conference: Definitions for Sepsis and Organ Dysfunction in Pediatrics," *Pediatric Crit Care Med* Jan. 2005 pp. 2-8, vol. 6(1) [abstract only].
Hack, E. et al. (Jul. 1992). "Interleukin-8 in relation to shock and inflammatory mediators", Infection and Immunity, *American Society for Microbiology*: 60(7): 2835-2842.
Hanley et al., "A method of comparing the areas under receiver operating characteristic curves derived from the same cases," *Radiology*, Sep. 1983, pp. 839-843, vol. 148(3).
Hanna, W. et al. (Apr. 2013, e-published Jan. 3, 2013). "Pediatric sepsis: challenges and adjunctive therapies," *Crit Care Clin* 29(2):203-222.
Hein, Ortrud Vargas et al., "Time course of endothelial damage in septic prediction of outcome", *Critical Care, Biomed Central Ltd.*, 9(4): R307-R314 (2005).
Kaplan et al., "Changes in peroxisome proliferator activated receptor-gamma activity in children with septic shock," *Intensive Care Med.*, Jan. 2010, pp. 123-130, vol. 36(1).
Kaplan, J.M. et al. (Mar. 2011). "Biomarker discovery and development in pediatric critical care medicine," *Pediatr Crit Care Med* 12(2):165-173.
Kartal, E.D. et al. (Jun. 2012, e-published Jun. 1, 2012). "Several Cytokines and Protein C Levels with the Apache II Scoring System for Evaluation of Patients with Sepsis," *Balkan Medical Journal* 29(2): 174-178.
Knox, D.B. et al. (May 2015, e-published Apr. 8, 2015). "Phenotypic clusters within sepsis-associated multiple organ dysfunction syndrome," *Intensive Care Med* 41(5):814-822.
Levy et al., "The Surviving Sepsis Campaign: results of an international guideline-based performance improvement program targeting severe sepsis," *Crit. Care Med.*, Feb. 2010, pp. 367-374, vol. 38(2).
Livaditi, O. et al. (Dec. 2006, e-published Mar. 26, 2007). "Neutrophil CD64 expression and serum IL-8: sensitive early markers of severity and outcome in sepsis," *Cytokine* 36(5-6):283-290.
Lokshin, A.E. et al. (Aug. 2006, e-published Jan. 24, 2006). "Circulating IL-8 and anti-IL-8 autoantibody in patients with ovarian cancer," *Gynecol Oncol* 12(2):244-251.
Marshall et al., "Biomarkers of sepsis," *Crit. Care Med.*, Jul. 2009, pp. 2290-2298, vol. 37(7) [abstract only].
Marshall, "Sepsis: rethinking the approach to clinical research," J. Leukoc. Biol., Mar. 2008, 471-482, vol. 83(3).
Maslove et al., "Gene expression profiling in sepsis: timing, tissue, and translational considerations," *Trends in Molecular Medicine*, Apr. 2014, pp. 204-213, vol. 20(4).
Mera, S. et al., "Multiplex cytokine profiling in patients with sepsis", *APMIS*, 119(2):155-163 (2010).
Muller et al., "Logistic regression and Cart in the analysis of multimarker studies," *Clin. Chim. Acta.*, Aug. 2008, pp. 1-6, vol. 394(1-2).
Nichol, A.D. et al. (2010). "Relative hyperlactatemia and hospital mortality in critically ill patients: a retrospective multi-centre study," *Crit. Care.* 14:R25, 9 pages.
Nowak et al., Admission Chemokine (C-C motif) Ligand 4 Levels Predict Survival in Pediatric Septic Shock, Pediatr. *Crit. Care Med.*, Mar. 2010, pp. 213-216, vol. 11(2).

Osuchowski et al., "Stratification is the key: inflammatory biomarkers accurately direct immunomodulatory therapy in experimental sepsis," *Crit. Care Med.*, May 2009, pp. 1567-1573, vol. 37(5).
Patent Cooperation Treaty, "International Preliminary Report on Patentability and Written Opinion" in corresponding International application No. PCT/US2013/025223, dated Aug. 12, 2014, 5 pgs.
Patent Cooperation Treaty, "International Search Report" in corresponding International application No. PCT/US2013/025223, dated May 30, 2013, 2 pgs.
Ranieri et al., "Drotrecogin alfa (activated) in adults with septic shock," *N. Engl. J. Med.*, May 31, 2012, pp. 2055-2064, vol. 366(22).
Russell et al., "Vasopressin versus norepinephrine infusion in patients with septic shock," *N. Engl. J. Med.*, Feb. 28, 2008, pp. 877-887, vol. 358(9).
Shanley et al., "Genome-Level Longitudinal Expression of Signaling Pathways and Gene Networks in Pediatric Septic Shock," *Mol Med*, Sep.-Oct. 2007, pp. 495-508, vol. 13(9-10).
Sharron et al., "Platelets Induce Apoptosis during Sepsis in a Contact-Dependent Manner That Is Inhibited by GPIIb/IIIa Blockade," *PLoS One*, Jul. 2012, p. e41549, vol. 7(7).
Solan et al., "A novel role for matrix metalloproteinase-8 in sepsis," *Crit Care Med.*, Feb. 2012, pp. 379-387, vol. 40(2).
Standage et al., Biomarkers for pediatric sepsis and septic shock, *Expert Rev. Anti Infect. Ther.*, 2011, pp. 71-79.
Steyerberg, E.W. et al. (Jan. 2010). "Assessing the performance of prediction models: a framework for traditional and novel measures," *Epidemiology* 21(1):128-138.
Sweeney et al., "Recombinant human activated protein C, package labeling, and hemorrhage risks," *Crit. Care Med.*, Jan. 2009, pp. 327-329, vol. 37(1).
Temple, R. et al. (Dec. 2010, e-published Oct. 13, 2010). "Enrichment of clinical study populations," *Clin Pharmacol Ther* 88(6):774-778.
Verboon-Maciolek, M.A. et al. (Mar. 2006). "Inflammatory mediators for the diagnosis and treatment of sepsis in early infancy," *Pediatr Res* 59(3):457-461.
Vermont C.L. et al. CC and CXC chemokine levels in children with meningococcal sepsis accurately mortality and disease severity, *Critical Care*, Biomed Central Ltd., 10(1):1-8 (2006).
Vincent et al., "Ten reasons why we should Not use severity scores as entry criteria for clinical trials or in our treatment decisions," *Crit. Care Med.*, Jan. 2010, pp. 283-287, vol. 38(1).
Wacharasint et al., "Normal-range blood lactate concentration in septic shock is prognostic and predictive," *Shock*, Jul. 2012, pp. 4-10, vol. 38(1).
Watson et al., "Scope and epidemiology of pediatric sepsis," *Pediatr Crit Care Med*, 2005, vol. 6(3), (Suppl.).
Wheeler et al., "Extracellular heat shock protein 60 (Hsp60) levels in children with septic shock," *Inflamm Res.*, May 2007, pp. 216-219, vol. 56(5) [abstract only].
Wheeler et al., "Extracellular hsp70 levels in children with septic shock," *Pediatr Crit Care Med.* May 2005, pp. 308-311 vol. 6(3) [abstract only].
Wheeler et al., "Serum Neutrophil Gelatinase-associated Lipocalin (NGAL) as a Marker of Acute Kidney Injury in Critically III Children with Septic Shock," *Crit Care Med.*, Apr. 2008, pp. 1297-1303, vol. 36(4).
Wong, H.R. et al. (Feb. 2015). "Developing a clinically feasible personalized medicine approach to pediatric septic shock," *Am J Respir Crit Care Med* 191(3):309-315.
Wong et al., "A Multibiomarker-Based Outcome Risk Stratification Model for Adult Septic Shock," *Critical Care Medicine*, Apr. 2014, pp. 781-789, vol. 42(4).
Wong et al. "The pediatric sepsis biomarker risk model", *Critical Care*, 16:R174(2012).
Wong et al., "Genome-level expression profiles in pediatric septic shock indicate a role for altered zinc homeostasis in poor outcome," *Physiol. Genomics.*, Jul. 18, 2007, pp. 146-155, vol. 30(2).
Wong et al., "Genomic expression profiling across the pediatric systemic inflammatory response syndrome, sepsis, and septic shock spectrum," *Crit. Care Med.*, May 2009, pp. 1558-1566, vol. 37(5).

(56) References Cited

OTHER PUBLICATIONS

Wong, H.R. et al. (Aug. 2008, e-published May 29, 2008). "Interleukin-8 as a stratification tool for interventional trials involving pediatric septic shock," *Am J Respir Crit Care Med* 178(3):276-282.

Wong et al., "Increased serum nitrite and nitrate concentrations in children with the sepsis syndrome," *Crit Care Med.*, May 1995, pp. 835-842, vol. 23(5) [abstract only].

Wong et al., "Plasma bactericidal/permeability-increasing protein concentrations in critically ill children with the sepsis syndrome," *Pediatr Infect Dis J.*, Dec. 1995, pp. 1087-1091, vol. 14(12) [abstract only].

Wong et al., "Testing the Prognostic Accuracy of the Updated Pediatric Sepsis Biomarker Risk Model," *PLoS One*, Jan. 2014, pp. e86242 (6 pgs.), vol. 9(1).

Wong et al., "The Temporal Version of the Pediatric Sepsis Biomarker Risk Model," *PLoS One*, Mar. 2014, pp. e92121 (7 pgs.), vol. 9(3).

Wong, "Pediatric septic shock treatment: new clues from genomic profiling," *Pharmacogenetics*, Oct. 2007, pp. 1287-1290, vol. 8(10).

Wynn et al., "The host response to sepsis and developmental impact," *Pediatrics.*, May 2010, pp. 1031-1041, vol. 125(5).

\* cited by examiner

PERSEVERE-II: REDEFINING THE PEDIATRIC SEPSIS BIOMARKER RISK MODEL WITH SEPTIC SHOCK PHENOTYPE

CROSS REFERENCE TO RELATED APPLICATION

The present application claims the benefit of priority under 35 U.S.C. § 119(e) to U.S. Provisional Application No. 62/170,957, PERSEVERE II: Redefining the Pediatric Sepsis Biomarker Risk Model with Septic Shock Phenotype, filed on Jun. 4, 2015, which is currently co-pending herewith and which is incorporated by reference in its entirety.

STATEMENT REGARDING FEDERALLY-SPONSORED RESEARCH

This invention was made with government support under GM064619, GM099773, GM108025, and TR000077 awarded by the National Institutes of Health. The government has certain rights in this invention.

FIELD OF THE INVENTION

The invention disclosed herein generally relates to the identification and validatation of clinically relevant, quantifiable biomarkers of diagnostic and therapeutic responses for blood, vascular, cardiac, and respiratory tract dysfunction.

BACKGROUND

Septic shock and severe sepsis represent a major public health problem in the United States, despite the development of increasingly powerful antibiotics and advanced forms of intensive care unit-based support modalities (see, e.g., Shanley, T. et al. *Sepsis*, $3^{rd}$ Ed., St. Louis, Mo., Mosby (2006)). Worldwide, septic shock affects millions of adults, killing approximately one in four (see, e.g., Dellinger, R. et al. *Crit. Care Med.* 36:296-327 (2008)). A recent study suggests that the incidence and the mortality rates of septic shock in adults are increasing in the United States (Dombrovskiy, V. et al. *Crit. Care Med.* 35:1244-50 (2007)).

Septic shock is also a major problem in the pediatric age group, as there are ~42,000 cases of pediatric septic shock per year in the United States alone, with a mortality rate of ~10% (see, e.g., Watson, R. et al. *Am. J. Respir. Crit. Care Med.* 167:695-701 (2003)). While the pediatric mortality rate is lower than that of adults, it nonetheless translates to more than 4,000 childhood deaths per year and countless years of lost productivity due to death at a young age. While this high number of pediatric deaths per year from septic shock indicates that more children die per year in the United States from septic shock as the primary cause than those children who die from cancer, funding specifically targeted toward pediatric septic shock is substantially lower than that for pediatric cancer.

Heterogeneity is a major feature of pediatric septic shock, including widely variable mortality risk [Hanna W, Wong H R (2013) Pediatric sepsis: challenges and adjunctive therapies. Crit Care Clin 29: 203-222. doi: 10.1016/j.ccc.2012.11.003]. In the absence of tools to accurately assess baseline mortality risk, clinicians have little objective information to benchmark septic shock outcomes, adjust for risk in analyses of clinical data, risk stratify patients for interventional clinical trials, and guide decisions on which patients need the most aggressive treatment, and which do not.

Reliable stratification of outcome risk is therefore fundamental to effective clinical practice and clinical research (Marshall *J. Leukoc. Biol.* 83:471-82 (2008)). A reliable and widely accepted outcome risk stratification tool specific for septic shock in pediatric patients would be beneficial for stratification for interventional clinical trials, better-informed decision making for individual patients, and as a metric for quality improvement efforts.

A recently published roadmap for future research in the field of sepsis encourages incorporation of biomarkers and enrichment strategies for clinical trials [Cohen et al. Sepsis: a roadmap for future research. Lancet Infect Dis 2015, 15(5):581-614]. Several programs of research are attempting to directly improve clinical care by providing tools to differentiate patients with septic shock on the basis of mortality risk, and on the basis of their clinical phenotype [Knox et al. Phenotypic clusters within sepsis-associated multiple organ dysfunction syndrome. Intensive Care Med 2015, 41(5):814-822; Wong et al. Developing a clinically feasible personalized medicine approach to pediatric septic shock. Am J Respir Crit Care Med 2015, 191(3):309-315; Wong H R, et al. A multibiomarker-based outcome risk stratification model for adult septic shock. Crit Care Med 2014, 42(4):781-789]. While differentiating between septic shock phenotypes might guide selection of treatments specific to the phenotypic characteristics, tools that inform clinicians in real time about mortality risk both within and across septic shock phenotypes can help determine who needs aggressive and potentially higher risk treatments and who does not.

The Pediatric Sepsis Biomarker Risk Model (PERSEVERE) estimates baseline 28-day mortality risk for children with septic shock [Wong et al. The pediatric sepsis biomarker risk model. Crit Care 2012, 16(5):R174; Alder M N, Lindsell C J, Wong H R: The pediatric sepsis biomarker risk model: potential implications for sepsis therapy and biology. Expert Rev Anti Infect Ther 2014, 12(7):809-816]. PERSEVERE is also described in U.S. Pat. No. 9,238,841.

PERSEVERE was derived using Classification and Regression Tree (CART) methodology, and the model incorporates a panel of biomarkers and age. The PERSEVERE biomarkers were selected objectively, using discovery oriented transcriptomic studies [Kaplan J M, Wong H R: Biomarker discovery and development in pediatric critical care medicine. Pediatr Crit Care Med 2011, 12(2):165-173]. PERSEVERE performs well when tested in a heterogeneous septic shock cohort [Wong et al: Testing the prognostic accuracy of the updated pediatric sepsis biomarker risk model. PLoS One 2014, 9(1):e862421, but it is unknown how PERSEVERE performs when applied to distinct clinical phenotypes of septic shock.

Thrombocytopenia-associated multiple organ failure (TA-MOF) has been proposed as an important clinical phenotype of septic shock, with high mortality that is potentially modifiable by plasma exchange [Nguyen et al. Intensive plasma exchange increases a disintegrin and metalloprotease with thrombospondin motifs-13 activity and reverses organ dysfunction in children with thrombocytopenia-associated multiple organ failure. Crit Care Med 2008, 36(10):2878-2887; Nguyen et al. Thrombocytopenia-associated multiple organ failure. In: Pediatric Critical Care Medicine: Basic Science and Clinical Practice. Edited by Wheeler D S, Wong H R, Shanley T P, vol. 3. New York: Springer; 2014: 481-492; Nguyen et al. Acquired ADAMTS-13 deficiency in pediatric patients with severe sepsis. Haematologica 2007, 92(1):121-124]. TAMOF is defined by new onset multiple organ failure with new onset thrombocytopenia. The mechanistic link between thrombocytopenia and organ failure is thought to involve a form of microangiopathy analogous to thrombotic thrombocytopenic purpura (TTP), including decreased levels of ADAMTS-13 (A Disintegrin And Metalloprotease with ThromboSpondin motifs) and increased von Willebrand factor activity [Nguyen T C, Carcillo J A: Understanding the role of von Willebrand factor and its cleaving protease ADAM TS13 in the pathophysiology of critical illness. Pediatr Crit Care Med 2007, 8(2):187-189]. ADAMTS-13 regulates microvascular thrombosis by cleaving large and ultra-large thrombogenic von Willebrand factor multimers into smaller, less thrombogenic forms. Preliminary experience suggests plasma exchange restores ADAMTS-13 levels and restores organ function in children with TAMOF, although an appropriately powered study has yet to be conducted.

SUMMARY

The present disclosure provides improved methods for risk stratifying pediatric septic shock patients and thereby also provides improved methods of treating septic shock. Prior to the instant disclosure, it was unknown whether the inventors' previously developed sepsis risk model, referred to as "PERSEVERE", was useful for risk stratifying patients when applied to distinct clinical phenotypes of septic shock, such as TAMOF and multiple organ failure (MOF) without new onset thrombocytopenia. The present invention is based, in part, on the examples provided herein which describe testing the performance of PERSEVERE in children with these distinct clinical phenotypes of septic shock and the revision of PERSEVERE to enhance its performance across all clinical phenotypes. The revised version of the model described herein is referred to as PERSEVERE-II.

In embodiments, the disclosure provides a method of treating septic shock in a pediatric patient, the method comprising identifying a pediatric patient with septic shock; obtaining at least one biological sample from the patient; determining the blood platelet count and the amount of each of the following protein biomarkers in the at least one biological sample: C-C chemokine ligand 3 (CCL3), heat shock protein 70 kDa 1B (HSPA1B), interleukin-8 (IL8), granzyme B (GZMB), and matrix metalloproteinase 8 (MMP8); classifying the patient as low, intermediate or high risk of mortality based on the blood platelet count and the amount of each of the protein biomarkers in the sample; and treating the intermediate or high risk patient with advanced treatment selected from the group consisting of extracorporeal membrane oxygenation/life support, plasmapheresis, plasma exchange, pulmonary artery catheterization, high volume continuous hemofiltration, and combinations thereof; and excluding the low risk patient from the aforementioned treatments.

In embodiments, the disclosure provides a method of classifying a pediatric patient with septic shock as having a high, intermediate, or low risk of mortality, the method comprising: identifying a pediatric patient with septic shock; obtaining a biological sample from the patient; determining the blood platelet count and the amount of each of the following protein biomarkers in the at least one biological sample: platelets, C-C chemokine ligand 3 (CCL3), heat shock protein 70 kDa 1B (HSPA1B), interleukin-8 (IL8), granzyme B (GZMB), and matrix metalloproteinase 8 (MMP8); and classifying the patient as low risk if any of the following are true:
a) an amount of CCL3 protein less than or equal to 150 pg/ml and an amount of HSPA1B protein less than or equal to 90,000 pg/ml (TN1), or
b) an amount of CCL3 protein less than or equal to 150 pg/ml, an amount of HSPA1B protein greater than 90,000 pg/ml, and an amount of IL8 protein less than or equal to 200 pg/ml (TN2), or
c) an amount of CCL3 protein less than or equal to 150 pg/ml, an amount of HSPA1B protein greater than 90,000 pg/ml, an amount of IL8 protein greater than 200 pg/ml, a platelet count greater than 38, an amount of IL8 protein less than or equal to 830 pg/ml, and an amount of MMP8 protein greater than 27,400 pg/ml (TN5), or
d) an amount of CCL3 protein greater than 150 pg/ml, a platelet count greater than 90, and an amount of GZMB protein less or equal to 32 pg/ml (TN8) or
e) an amount of CCL3 protein greater than 150 pg/ml, a platelet count greater than 90, an amount of GZMB protein greater than 32 pg/ml, an amount of HSPA1B protein less than or equal to 1.6×10E6 pg/ml, and an amount of IL8 protein less than 3,350 pg/ml; (TN9)
classifying the patient as intermediate risk if any of the following are true:
f) an amount of CCL3 protein less than or equal to 150 pg/ml, a amount of HSPA1B greater than 90,000 pg/ml, an amount of IL8 protein greater than 200 pg/ml, a platelet count greater than 38, an amount of IL8 protein less than or equal to 830 pg/ml, and an amount of MMP8 protein less than or equal to 27,400 pg/ml (TN4), or
g) an amount of CCL3 protein less than or equal to 150 pg/ml, a amount of HSPA1B protein greater than 90,000 pg/ml, an amount of IL8 protein greater than 200 pg/ml, a platelet count greater than 38, and an amount of 1L8 protein greater than 830 pg/ml (TN6), or
h) an amount of CCL3 protein greater than 150 pg/ml, and a platelet count less than or equal to 90 (TN7), or
i) an amount of CCL3 protein greater than 150 pg/ml, a platelet count greater than 90, an amount of GZMB protein greater than 32 pg/ml, an amount of HSPA1B protein less than or equal to 1.6×10E6 pg/ml, and an amount of IL8 protein greater than 3,350 pg/ml. (TN10); and
classifying the patient as high risk if any of the following are true:
j) an amount of CCL3 protein less than or equal to 150 pg/ml, an amount of HSPA1B protein greater than 90,000 pg/ml, an amount of IL8 protein greater than 200 pg/ml, and a platelet count less than or equal to 38 (TN3).
k) an amount of CCL3 protein greater than 150 pg/ml, a platelet count greater than 90, an amount of GZMB protein greater than 32 pg/ml, and an amount of HSPA1B protein greater than 1.6×10E6 pg/ml (TN11).

In embodiments, the disclosure provides a method for stratifying septic shock patients based on baseline mortality risk, the method comprising classifying a pediatric patient with septic shock as having a high, intermediate, or low risk of mortality using the methods described herein.

In embodiments of any of the methods described here, the classifying is performed using a classification and regression tree methodology.

In embodiments of any of the methods described here, the septic shock is a distinct clinical phenotype of septic shock. In embodiments, the distinct clinical phenotype of septic shock is multiple organ failure in the absence of new onset thrombocytopenia. In embodiments, the distinct clinical phenotype of septic shock is thrombocytopenia-associated multiple organ failure (TAMOF).

In embodiments of any of the methods described here, the sample is obtained within the first hour of presentation with septic shock. In embodiments, the sample is obtained within the first 48 hours of presentation with septic shock.

In embodiments of any of the methods described here, the method of classifying a patient with septic shock is independent of thrombocytopenia-associated multiple organ failure and multiple organ failure.

In embodiments of any of the methods described here, the protein biomarkers are blood proteins and the biological sample is whole blood or plasma, or a comination thereof.

In embodiments, the methods described here further comprise incorporating additional patient data, such as co-morbidities, age, gender, and/or patient-reported ethnicity. In some embodiments, the methods further comprise incorporating additional patient clincial data, such as indicia of septic shock including the septic shock causative organism and the presence or absence multiple organ failure. In embodiments, the multiple organ failure is thrombocytopenia-associated multiple organ failure.

In embodiments, the determination of whether the level(s) of the one or more biomarkers are elevated above a cut-off level can be combined with one or more additional population-based risk scores. In some embodiments, the one or more population-based risk scores includes PRISM, PIM, and/or PELOD.

In embodiments, the biological sample is obtained within the first hour of presentation with septic shock. In embodiments, the biological sample is obtained within the first 8 hours of presentation with septic shock. In embodiments, the sample is obtained within the first 24 hours of presentation with septic shock. In embodiments, the sample is obtained within the first 48 hours of presentation with septic shock.

Embodiments of the invention also encompass methods of providing individualized treatment for a pediatric patient with septic shock, wherein the patient is classified as high, intermediate, or low risk via the methods described herein. In general, patients identified as at high or intermediate risk for mortality are administered one or more advanced therapies selected from the group consisting of extracorporeal membrane oxygenation/life support, plasmapheresis, pulmonary artery catheterization, and/or high volume continuous hemofiltration. A patient classified as low risk is excluded from the above therapies.

Embodiments of the invention also encompass methods of selecting a pediatric patient with septic shock for a clinical trial, wherein a patient classified as high or intermediate risk via the methods described herein can be selected for a moderate or high risk clinical trial, and wherein a patient classified as low risk via the methods described herein can be excluded from a moderate or high risk clinical trial.

Embodiments of the invention also encompass methods of predicting illness severity in a pediatric patient with septic shock, wherein a patient classified as high or intermediate risk via the methods described herein can be classified as having a severe or moderately severe case of septic shock and a patient classified as low risk can be classified as having a less severe case of septic shock.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Figure 1:
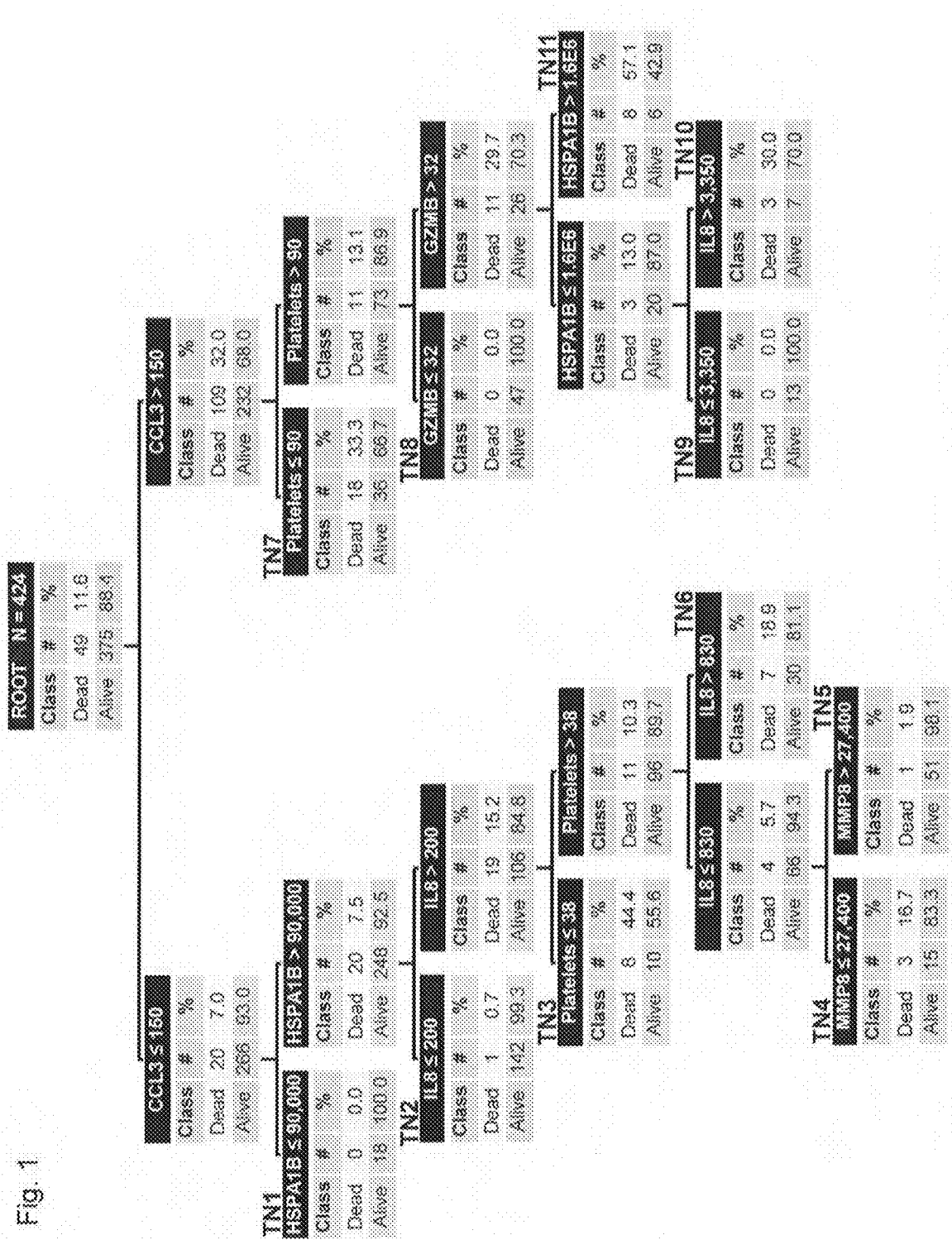
FIG. 1 shows PERSEVERE-II. The top node of the decision tree, the root node, provides the total number of subjects and the number and proportion of survivors and nonsurvivors. Each daughter node provides the criterion for deciding subsequent partitions, along with the number and proportion of survivors and nonsurvivors. Terminal nodes reflect the final assignment of risk to an individual case. Terminal nodes are numbered in bold.

The present disclosure is based upon improvements in a previously reported pediatric sepsis biomarker risk model (PERSEVERE) for estimating baseline 28-day mortality risk in children with septic shock. The model utilizes classification and regression tree methodology, and incorporates age along with a panel of biomarkers which were selected objectively, using discovery oriented transcriptomic studies. The present disclosure provides an improved model, referred to as PERSEVERE-II, which performs well when applied to different clinical phenotypes of septic shock. The methods described here are based, in part, on the discovery of the importance of platelet count in driving the classification.

Unless otherwise noted, terms are to be understood according to conventional usage by those of ordinary skill in the relevant art.

As used herein, the term "sample" encompasses a biological sample obtained from a subject or patient. In embodiments, the sample is a blood sample.

As used herein, "blood" can include, for example, plasma, serum, whole blood, blood lysates, and the like. In embodiments, the blood sample is a whole blood.

As used herein, the term "assessing" includes any form of measurement, and includes determining if an element is present or not. The terms "determining," "measuring," "evaluating," "assessing" and "assaying" can be used interchangeably and can include quantitative and/or qualitative determinations.

As used herein, the term "diagnosing or monitoring" with reference to septic shock refers to a method or process of determining if a subject has or does not have septic shock or determining the severity or degree of septic shock.

As used herein, "outcome" can refer to the primary outcome studied, typically 28-day survival/mortality. The importance of survival/mortality in the context of pediatric septic shock is readily evident. The common choice of 28 days was based on the fact that 28-day mortality is a standard primary endpoint for interventional clinical trials involving critically ill patients.

As used herein, "outcome" can also refer to the secondary outcome studied, namely resolution of organ failure after 14 days or 28 days or limb loss. Although mortality/survival is obviously an important outcome, survivors have clinically relevant short- and long-term morbidities that impact quality of life, which are not captured by the dichotomy of "alive" or "dead." In the absence of a formal, validated quality of life measurement tool for survivors of pediatric septic shock, resolution of organ failure was tracked as a secondary outcome measure. Specifically, the presence or absence of new organ failure over two timeframes was tracked: 14 days after admission and 28 days after admission. Patients having organ failure beyond 28 days are likely to survive with significant morbidities having negative consequences for quality of life. Organ failure was defined based on published and well-accepted criteria for the pediatric population (Goldstein, B. et al. *Pediatr. Crit. Care Med.* 6:208 (2005)). Specifically, cardiovascular, respiratory, renal, hepatic, hematologic, and neurologic failure were tracked. In addition, limb loss was tracked as a secondary outcome. Although limb loss is not a true "organ failure," it is an important consequence of pediatric septic shock with obvious impact on quality of life.

As used herein, the terms "predicting outcome" and "outcome risk stratification" with reference to septic shock refers to a method or process of prognosing a patient's risk of a certain outcome. In some embodiments, predicting an outcome relates to determining a relative risk of mortality. Such mortality risk can be high risk, moderate risk, moderate-high risk, moderate-low risk, or low risk. Alternatively, such mortality risk can be described simply as high risk or low risk, corresponding to high risk of death or high likelihood of survival, respectively. As related to the terminal nodes of the decision trees described herein, a "high risk terminal node" corresponds to a high mortality probability, whereas a "low risk terminal node" corresponds to a low mortality proability.

As used herein, the term "high risk clinical trial" refers to one in which the test agent has "more than mininal risk" (as defined by the terminology used by institutional review boards, or IRBs). In some embodiments, a high risk clinical trial is a drug trial.

As used herein, the term "low risk clinical trial" refers to one in which the test agent has "minimal risk" (as defined by the terminology used by IRBs). In some embodiments, a low risk clinical trial is one that is not a drug trial. In some embodiments, a low risk clinical trial is one that that involves the use of a monitor or clinical practice process. In some embodiments, a low risk clinical trial is an observational clinical trial.

As used herein, the terms "modulated" or "modulation," or "regulated" or "regulation" and "differentially regulated" can refer to both up regulation (i.e., activation or stimulation, e.g., by agonizing or potentiating) and down regulation (i e , inhibition or suppression, e.g., by antagonizing, decreasing or inhibiting), unless otherwise specified or clear from the context of a specific usage.

As used herein, the term "subject" refers to any member of the animal kingdom. In some embodiments, a subject is a human patient. In some embodiments, a subject is a pediatric patient. In some embodiments, a pediatric patient is a patient under 18 years of age, while an adult patient is 18 or older.

As used herein, the terms "treatment," "treating," "treat," and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" can also encompass delivery of an agent or administration of a therapy in order to provide for a pharmacologic effect, even in the absence of a disease or condition.

As used herein, the term "marker" or "biomarker" refers to a biological molecule, such as, for example, a nucleic acid, peptide, protein, hormone, and the like, whose presence or concentration can be detected and correlated with a known condition, such as a disease state. It can also be used to refer to a differentially expressed gene whose expression pattern can be utilized as part of a predictive, prognostic or diagnostic process in healthy conditions or a disease state, or which, alternatively, can be used in methods for identifying a useful treatment or prevention therapy.

As used herein, the term "decision tree" refers to a standard machine learning technique for multivariate data analysis and classification. Decision trees can be used to derive easily interpretable and intuitive rules for decision support systems. In developed countries with ready access to powerful antibiotics and modern intensive care units, septic shock continues to be a major cause of morbidity and mortality in both adult and pediatric populations (Czaja, A., et al. *Pediatrics,* 123:849-57 (2009); Dellinger, R., et al. *Crit. Care Med.,* 36:296-327 (2008); Dombrovskiy, V., et al. *Crit. Care Med.,* 35:1244-50 (2007); Watson, R., et al. *Am. J. Resp. Crit. Care Med.,* 167:695-701 (2003)). Septic shock is a highly heterogeneous syndrome having variable expression in a given patient cohort. Dating from the 1990s, many clinical trials have been conducted to evaluate potential novel therapies for septic shock, and experimental therapies continue to be evaluated. However, with the exception of one therapy which briefly gained an FDA-approved specific labeling for septic shock in adults, namely activated protein C, the majority of experimental therapies fail to demonstrate efficacy when tested in randomized, controlled trials, despite being based on sound biological principles and quality preclinical data (see, e.g., Sweeney, D. et al. *Intensive Care Med.* 37:666-88 (2009); Marshall, J. *J. Leukoc. Biol.,* 82:471-82 (2008)). The above-mentioned activated protein C therapy, namely Xigris (Eli Lilly, Indianapolis, Ind.), has been taken off the market by the manufacturer because a large trial in Europe failed to demonstrate efficacy.

While failure is likely multi-factorial, one consistent confounder is that septic shock is not a simple disease with uniform expression across a given patient cohort. Rather, septic shock is a complex syndrome displaying a tremendous degree of heterogeneity. The intrinsic heterogeneity of clinical septic shock is a major challenge. For clinical trials, individual patient management, and quality improvement efforts, it is unclear which patients are least likely to survive and thus benefit from alternative treatment approaches. Because the inability to manage this heterogeneity presents a major challenge for effective and rational clinical trials, a robust risk stratification tool could overcome this challenge (Marshall, J. *J. Leukoc. Biol.,* 82:471-82 (2008); Marshall, J. et al. *Crit. Care Med.,* 37:2290-8 (2009)).

In the pediatric age group, a randomized trial of activated protein C was terminated early due to futility (Nadel, S. et al. *Lancet* 369:836-43 (2007)). Thus, septic shock therapy for the pediatric age group is limited solely to prevention (such as vaccines), antibiotics, and intensive care unit-based organ support (see, e.g., Shanley, T. et al. *Sepsis,* 3$^{rd}$ Ed., St. Louis, Mo., Mosby (2006); Brierley, J., et al. *Crit. Care Med.* 37:666-88 (2009)). The reason for failure in clinical trials is presumably not because the biological/physiological principle being tested was fundamentally flawed. Rather, the primary reason for failure lies in the inability to effectively address the substantial heterogeneity that characterizes the syndrome of septic shock. Septic shock is a heterogeneous syndrome with the potential to negatively and directly affect all organ systems relevant to this challenge topic, including blood (coagulopathy), vascular (distributive shock), cardiac (cardiogenic shock), and respiratory (acute respiratory distress syndrome) function. The heterogeneity of septic shock has consistently challenged multiple investigators attempting to evaluate the efficacy of various experimental interventions.

A key challenge in the field is therefore to reduce and manage this heterogeneity by more effectively stratifying patients for the purposes of more rational and effective clinical research and clinical management. An effective stratification process with some qualitative metric could inform decision-making and improve patient outcomes and prospective clinical trial design and management.

The concept of pre-intervention stratification in sepsis, and its positive impact on the efficacy of an experimental therapy, has been corroborated in a murine model of polymicrobial sepsis (Osuchowski, M. et al. Crit. Care Med. 37:1567-73 (2009)). While this study provides proof-of-concept, translating the concept to the bedside of critically ill patients remains a major challenge.

The ability to predict outcome, for individual patients and early in the course of illness, would be a major advancement in clinicians' ability to conduct septic shock interventional clinical trials in a more effective manner While models that generate mortality prediction scores based on physiological variables, such as the Acute Physiology and Chronic Health Evaluation (APACHE) and Pediatric RIsk of Mortality (PRISM) models, can be very effective for estimating population-based outcome risks, these tools are not intended for stratification of individual patients.

A blood protein-derived profile of multiple candidate biomarkers is a clinically feasible and effective strategy for meeting this challenge. Based on a set of biomarkers, selected in an objective and relatively unbiased manner, a multi-biomarker-based risk model was generated to predict individual patient outcome and illness severity. This model was described previously and is referred to as PERSEVERE: PEdiatRic SEpsis biomarkEr Risk model. See Wong et al. The pediatric sepsis biomarker risk model. Crit Care 2012, 16(5):R174; Alder M N, Lindsell C J, Wong H R: The pediatric sepsis biomarker risk model: potential implications for sepsis therapy and biology. Expert Rev Anti Infect Ther 2014, 12(7):809-816; and U.S. Pat. No. 9,238,841. This model is capable of robustly predicting outcomes, with high sensitivity. When PERSEVERE was applied to an independent cohort of children with septic shock, those predicted as non-survivors had more than 25% mortality by 28 days. Conversely, those predicted as survivors had more than 97% survival by 28 days. Additionally, the high-risk survivors in the updated model were found to have a greater degree of illness severity as measured by persistence of organ failure, pediatric intensive care unit (PICU) length of stay (LOS), and PICU-free days. PERSEVERE has proven to be effective in derivation and test cohorts and can be used to augment population-based risk scores, such as APACHE and PRISM.

The feasibility of a biomarker-based approach to stratification of pediatric patients early in the course of illness has been demonstrated (Wong, H. et al. Am. J. Respir. Crit. Care Med. 178:276-82 (2008)). This study demonstrated that a specific serum interleukin-8 (IL8) cut-off level, obtained within 24 hours of presentation to the pediatric intensive care unit, has a 95% negative predictive value for mortality in children with septic shock who were receiving standard care (confidence interval of 90 to 98%; likelihood ratio of 0.4 with confidence interval of 0.2 to 0.7). In contrast to the many previous studies describing measurements of cytokines and other mediators in children with septic shock (see, e.g., Wong, H. et al. Crit. Care Med. 23:835-42 (1995); Wong, H. et al. J. Ped. Infect. Dis. 14:1087-91 (1995); Wheeler, D. et al. Ped. Crit. Care Med. 6:308-11 (2005); Wheeler, D. et al. Inflamm. Res. 56:216-9 (2007); Giuliano, Jr., J. et al. Shock 28:650-4 (2007); Wheeler, D. et al. Crit. Care Med. 36:1297-1303 (2008); Kaplan, J. et al. Intensive Care Med. 36:123-30 (2010); Nowak, J. et al. Ped. Crit. Care Med. 11:213-6 (2010)), these IL8 data were prospectively validated across two independent, large test cohorts of children with septic shock.

Based on these data, the use of IL8 alone to exclude pediatric patients from septic shock interventional clinical trials that carry more than minimal risk was exploited to generate a predictive model. This model performed better than PRISM; however, despite an excellent negative predictive value, the positive predictive value of the IL8 cut-off was lacking, meaning that considering IL8 in isolation does not sufficiently discriminate between patients who are likely to survive and those who are not; sensitivity and specificity for this model were also not very robust. As described previously, use of an expanded panel of biomarkers in the original PERSEVERE model improved both negative and positive predictive capability.

Like its predecessor, the PERSEVERE-II model allows for more effective risk stratification of pediatric patients for the conduct of clinical trials by improving the risk to benefit ratio of a given experimental therapy by allowing for effective exclusion of pediatric patients having a high probability of survival with standard care. This approach is particularly important for experimental therapies that carry significant risks for serious adverse events, as previously demonstrated (Wong, H. et al. Am. J. Respir. Crit. Care Med. 178:276-82 (2008)). Like its predecessor, PERSEVERE-II also allows for the effective inclusion of pediatric patients having a high risk of mortality. This approach is particularly important for trials having mortality as the primary outcome measure. This is also referred to as 'prognostic enrichment'. By effectively selecting a subpopulation with a relatively high mortality risk, the sample size required for acceptable statistical power could be effectively lowered. As clinical trial expenditures increase, the need to minimize required sample size becomes increasingly important.

PERSEVERE-II also allows for more rational application of current and future high risk therapies for individual children with septic shock, outside of the clinical trial context. For example, high risk but potentially effective therapies, such as extracorporeal membrane oxygenation/life support, plasmapheresis, pulmonary artery catheterization, and high volume continuous hemofiltration, are widely applied as "last ditch" efforts in pediatric septic shock. PERSEVERE-II allows for a more objective and timely selection of pediatric patients for these high risk therapies, thus increasing the probability of success.

The original PERSEVERE infrastructure, on which PERSEVERE-II is also based, has been described previously. In brief, an annotated clinical database called Protocol Manager was linked to a Biological Specimen Tracking System (BSTS), which is web-based and was developed locally. Protocol Manager is web-enabled such that the collaborating centers can capture and directly enter data at the local level. All Division of Pediatric Informatics (Cincinnati Children's Hospital Medical Center) data collection systems incorporated a multi-layered data security approach through the use of roles, user accounts, and passwords. Secure data were protected by a firewall system. All annotated clinical data were de-identified and patients were assigned a unique research number for database queries; these research numbers were linked to samples via bar codes using the BSTS. The database was not de-identified with respect to disease process, outcomes, and clinical data. In fact, the database contains extensive clinical data (co-morbid conditions, medications, laboratory values, microbiology studies, outcomes, etc.), which allow biological data to be analyzed in the context of important clinical phenotypes. The database and the program's standard operating procedures were designed to ensure capture and entry of valid clinical data, with multiple strategies and cross-checks to ensure the validity of the clinical data.

The identification of biomarkers, model derivation, and validation of the original PERSEVERE was also been described previously, see Wong et al. The pediatric sepsis biomarker risk model. Crit Care 2012, 16(5):R174; Alder M N, Lindsell C J, Wong H R: The pediatric sepsis biomarker risk model: potential implications for sepsis therapy and biology. Expert Rev Anti Infect Ther 2014, 12(7):809-816; and U.S. Pat. No. 9,238,841. Briefly, candidate biomarkers were selected objectively, using discovery oriented transcriptomic studies. The original model was derived using 12 candidate genes. A decision tree was developed through a binary recursive partitioning algorithm, and 2 x 2 contingency tables were assembled, showing true positives, true negatives, false positives, and false negatives. The model describes the relationship between the 12 identified biomarkers, clinical data including the PRISM score, and outcomes. Refinements yielded a 5-biomarker, 5-decision rule, 10-daughter node classification tree. Three biomarkers, CCL3, HSPA1B, and IL8, were found to be the primary predictors. The model was prospectively evaluated in a separate, independent test cohort of children with septic shock. Prospective validation of a derived risk model is a standard and required approach to rigorous clinical investigations. The feasibility of prospectively validating biomarker-based risk models in the context of pediatric septic shock has been previously demonstrated (Wong, H. et al. *Am. J. Respir. Crit. Care Med.* 178:276-82 (2008)).

In embodiments, the methods described here are useful in clinical trial enrollment, clinical research, and management. The sickest patients can be identified via the model described here based on their mortality risk, and these patients can then be selected for high risk interventions, while the low risk patients can be excluded from such high risk interventions. The net result is the generation of a study population with a more favorable risk to benefit ratio. The methods described here can also be used to stratify pediatric septic shock patients for low risk clinical trials. The effects of the low risk intervention can be assessed post-hoc based on risk stratification. The least sick patients can be identified via the model based on the likelihood of a positive outcome, and these patients can then be selected for low risk interventions.

In embodiments, the methods described here are useful for selecting participants for interventional clinical trials. Excluding participants with very low mortality risk, while simultaneously selecting those at greatest mortality risk, increases the magnitude of possible survival benefit of a new therapy, while not placing those most likely to survive at risk of any adverse effects of a new therapeutic approach. This may also be referred to as 'prognostic enrichment'. By stratifying patients via the methods described here, it is possible to optimize the risk-to-benefit ratio of a test agent having more than minimal risk, and consequently conduct more rational clinical trials.

In embodiments, the methods described here are useful in clinical decision support, e.g., to decide which patients are more likely to benefit from high risk, invasive therapeutic and support modalities used in the treatment of septic shock, such as extracorporeal membrane oxygenation/life support, plasmapheresis, pulmonary artery catheterization, and high volume continuous hemofiltration. In addition, differences in illness severity in those who survived but who were predicted to die, and in those who survived and were predicted to survive, could provide some clues to tailoring treatments to improve outcomes for all pediatric septic shock patients. The methods provided by the disclosure can therefore also be used in point of care decision-making for individual patients.

In embodiments, the methods described here are useful for quality improvement by serving as a metric for institutions to measure their respective outcomes in pediatric patients with septic shock. If a substantial number of these patients are actually dying, then this could serve as a trigger to examine their clinical processes. Alternatively, if an institution has a large number of high risk pediatric patients who are actually surviving, then the present methods can be used to study those patients.

In an exemplary embodiment, the outcome risk stratification method is carried out on a patient to predict an outcome for a pediatric patient with septic shock. A serum sample is obtained from a pediatric patient. Serum concentrations of C-C chemokine ligand 3 (CCL3), heat shock protein 70 kDa 1B (HSPA1B), interleukin-8 (IL8), granzyme B (GZMB), and matrix metalloproteinase 8 (MMP8) are then measured (e.g. using a magnetic bead multi-plex platform and a Luminex® 100/200 System). The patient's platelet count is also measured. The results of the protein biomarker assays are then combined with the patient's platelet count and used to assess mortality risk according to the methods described here.

In embodiments, a pediatric patient with septic shock is evaluated via the outcome risk stratification method described herein by subjecting the patient to the decision tree depicted in FIG. 1. In embodiments, a patient in one of the low risk terminal nodes of the decision tree is determined to have a low risk of mortality. In embodiments, a low risk of mortality indicates a probability of mortality ranging from 0% to 7%, from 0% to 5%, or from 0% to 3%, or from 0% to 2%. In embodiments, a low risk of mortality indicates a probability of mortality less than 5%, less than 3%, less than 2%, or less than 1.5%. In embodiments, a patient in one of the intermediate risk nodes of the decision tree is determined to have an intermediate risk of mortality. In embodiments, an intermediate risk of mortality indicates a probability of mortality ranging from 15% to 35%, or from 10-25%. In embodiments, a patient in one of the high risk nodes of the decision tree is determined to have a high risk of mortality. In embodiments, a high risk of mortality indicates a probability of mortality greater than 40%, greater than 45%, greater than 50%, or greater than 55%.

Sample Acquisition

Stratification of patients presenting with septic shock becomes increasingly difficult as time progresses due to the inherently acute symptoms of septic shock. Accordingly, the methods described herein which allow for stratification of individual pediatric patients in order to determine the patient's outcome risk involve acquiring a sample from a pediatric patient early in the patient's course of diagnosis and treatment.

In some embodiments, a sample is acquired from a pediatric patient within the first 60 minutes of presentation with septic shock. In some embodiments, a sample is acquired from a pediatric patient within the first 8 hours of presentation with septic shock. In some embodiments, a sample is acquired from a pediatric patient within the first 24 hours of presentation with septic shock. In some embodiments, a sample is acquired from a pediatric patient within the first 48 hours of presentation with septic shock. In some embodiments, a sample is acquired from a pediatric patient within the first 72 hours of presentation with septic shock.

In some embodiments, a sample is acquired from a pediatric patient within the first 1, 2, 3, 4, 5, 6, 7, 8, 9, or 10 hours of presentation with septic shock. In some embodiments, a sample is acquired from a pediatric patient within the first 11, 12, 13, 14, 15, 16, 17, 18, 19, or 20 hours of presentation with septic shock. In some embodiments, a sample is acquired from a pediatric patient within the first 21, 22, 23, 24, 25, 26, 27, 28, 29, or 30 hours of presentation with septic shock. In some embodiments, a sample is acquired from a pediatric patient within the first 31, 32, 33, 34, 35, 36, 37, 38, 39, or 40 hours of presentation with septic shock. In some embodiments, a sample is acquired from a pediatric patient within the first 41, 42, 43, 44, 45, 46, 47, 48, 49, or 50 hours of presentation with septic shock. In some embodiments, a sample is acquired from a pediatric patient within the first 51, 52, 53, 54, 55, 56, 57, 58, 59, or 60 hours of presentation with septic shock. In some embodiments, a sample is acquired from a pediatric patient within the first 61, 62, 63, 64, 65, 66, 67, 68, 69, or 70 hours of presentation with septic shock. In some embodiments, a sample is acquired from a pediatric patient within the first 71, 72, 73, 74, 75, 76, 77, 78, 79, or 80 hours of presentation with septic shock.

Additional Patient Information

The demographic data, clinical characteristics, and/or results from other tests or indicia of septic shock specific to a pediatric patient with septic shock can affect the patient's outcome risk. Accordingly, such demographic data, clinical characteristics, and/or results from other tests or indicia of septic shock can be incorporated into the methods described herein which allow for stratification of individual pediatric patients in order to determine the patient's outcome risk. Such demographic data, clinical characteristics, and/or results from other tests or indicia of septic shock can also be used in combination with the methods described herein which allow for stratification of individual pediatric patients in order to determine the patient's outcome risk.

Such pediatric patient demographic data can include, for example, the patient's age, race, gender, and the like.

In some embodiments, the biomarker-based risk stratification model described herein can incorporate the patient's age to determine an outcome risk. In some embodiments, the biomarker-based risk stratification model described herein can incorporate the patient's race to determine an outcome risk. In some embodiments, the biomarker-based risk stratification model described herein can incorporate the patient's gender to determine an outcome risk.

In some embodiments, the biomarker-based risk stratification model described herein can be used in combination with the patient's age to determine an outcome risk. In some embodiments, the biomarker-based risk stratification model described herein can be used in combination with the patient's race to determine an outcome risk. In some embodiments, the biomarker-based risk stratification model described herein can be used in combination with the patient's gender to determine an outcome risk.

Such patient clinical characteristics and/or results from other tests or indicia of septic shock can include, for example, the patient's co-mobidities and/or septic shock causative organism, and the like.

Patient co-morbidities can include, for example, acute lymphocytic leukemia, acute myeloid leukemia, aplastic anemia, atrial and ventricular septal defects, bone marrow transplantation, caustic ingestion, chronic granulomatous disease, chronic hepatic failure, chronic lung disease, chronic lymphopenia, chronic obstructive pulmonary disease (COPD), congestive heart failure (NYHA Class IV CHF), Cri du Chat syndrome, cyclic neutropenia, developmental delay, diabetes, DiGeorge syndrome, Down syndrome, drowning, end stage renal disease, glycogen storage disease type 1, hematologic or metastatic solid organ malignancy, hemophagocytic lymphohistiocytosis, hepatoblastoma, heterotaxy, hydrocephalus, hypoplastic left heart syndrome, IPEX Syndrome, kidney transplant, Langerhans cell histiocytosis, liver and bowel transplant, liver failure, liver transplant, medulloblastoma, metaleukodystrophy, mitochondrial disorder, multiple congenital anomalies, multivisceral transplant, nephrotic syndrome, neuroblastoma, neuromuscular disorder, obstructed pulmonary veins, Pallister Killian syndrome, Prader-Willi syndrome, requirement for chronic dialysis, requirement for chronic steroids, retinoblastoma, rhabdomyosarcoma, rhabdosarcoma, sarcoma, seizure disorder, severe combined immune deficiency, short gut syndrome, sickle cell disease, sleep apnea, small bowel transplant, subglottic stenosis, tracheal stenosis, traumatic brain injury, trisomy 18, type 1 diabetes mellitus, unspecified brain tumor, unspecified congenital heart disease, unspecified leukemia, VATER Syndrom, Wilms tumor, and the like. Any one or more of the above patient co-morbidities can be indicative of the presence or absence of chronic disease in the patient.

Septic shock causative organisms can include, for example, *Acinetobacter baumannii*, Adenovirus, *Bacteroides* species, *Candida* species, *Capnotyophaga jenuni*, Cytomegalovirus, *Enterobacter cloacae*, *Enterococcus faecalis*, *Escherichia coli*, Herpes simplex virus, Human metapneumovirus, Influenza A, *Klebsiella pneumonia*, *Micrococcus* species, mixed bacterial infection, *Moraxella catarrhalis*, *Neisseria meningitides*, Parainfluenza, *Pseudomonas* species, *Serratia marcescens, Staphylococcus aureus, Streptococcus agalactiae, Streptococcus milleri, Streptococcus pneumonia, Streptococcus pyogenes*, unspecified gram negative rods, unspecified gram positive cocci, and the like.

In some embodiments, the biomarker-based risk stratification model described herein can incorporate the patient's co-morbidities to determine an outcome risk. In some embodiments, the biomarker-based risk stratification model described herein can incorporate the patient's septic shock causative organism to determine an outcome risk.

In some embodiments, the biomarker-based risk stratification model described herein can be used in combination with the patient's co-morbidities to determine an outcome risk. In some embodiments, the biomarker-based risk stratification model described herein can be used in combination with the patient's septic shock causative organism to determine an outcome risk.

Population-Based Risk Scores

A number of models that generate mortality prediction scores based on physiological variables have been developed to date. These can include the APACHE, PRISM, Pediatric Index of Mortality (PIM), and/ pediatric logistic organ dysfunction (PELOD) models, and the like. The APACHE model considered can be APACHE I, APACHE II, APACHE III, APACHE IV, or a subsequent iteration of APACHE.

Such models can be very effective for estimating population-based outcome risks but are not intended for stratification of individual patients. The methods described herein which allow for stratification of individual patients can be used alone or in combination with one or more existing population-based risk scores.

In some embodiments, the biomarker-based risk stratification model described herein can be used with one or more additional population-based risk scores. In some embodiments, the biomarker-based risk stratification model described herein can be used in combination with PRISM. In some embodiments, the biomarker-based risk stratification model described herein can be used in combination with PIM. In some embodiments, the biomarker-based risk stratification model described herein can be used in combination with PELOD. In some embodiments, the biomarker-based risk stratification model described herein can be used in combination with a population-based risk score other than PRISM, PELOD, and PRISM.

High Risk Therapies

High risk, invasive therapeutic and support modalities can be used to treat septic shock. The methods described herein which allow for stratification of individual pediatric patients in order to determine the patient's outcome risk can help inform clinical decisions regarding the application of high risk therapies to specific pediatric patients, based on the patient's outcome risk.

High risk therapies include, for example, extracorporeal membrane oxygenation/life support, plasmapheresis, pulmonary artery catheterization, high volume continuous hemofiltration, and the like.

In some embodiments, individualized treatment can be provided to a pediatric patient by selecting a pediatric patient classified as high risk by the methods described herein for one or more high risk therapies. In some embodiments, individualized treatment can be provided to a pediatric patient by excluding a pediatric patient classified as low risk from one or more high risk therapies.

Certain embodiments of the invention include using quantification data from a gene-expression analysis and/or from a mRNA analysis, from a sample of blood, urine, saliva, broncho-alveolar lavage fluid, or the like. Embodiments of the invention include not only methods of conducting and interpreting such tests but also include reagents, kits, assays, and the like, for conducting the tests.

Diagnostic-testing procedure performance is commonly described by evaluating control groups to obtain four critical test characteristics, namely positive predictive value (PPV), negative predictive value (NPV), sensitivity, and specificity, which provide information regarding the effectiveness of the test. The PPV of a particular diagnostic test represents the proportion of subjects with a positive test result who are correctly diagnosed; for tests with a high PPV, a positive test indicates the presence of the condition in question. The NPV of a particular diagnostic test represents the proportion of subjects with a negative test result who are correctly diagnosed; for tests with a high NPV, a negative test indicates the absence of the condition. Sensitivity represents the proportion of correctly identified subjects who are actual positives; for tests with high sensitivity, a positive test indicates the presence of the condition in question. Specificity represents the proportion of correctly identified subjects who are actual negatives; for tests with high specificity, a negative test indicates the absence of the condition.

The threshold for the disease state can alternatively be defined as a 1-D quantitative score, or diagnostic cutoff, based upon receiver operating characteristic (ROC) analysis. The quantitative score based upon ROC analysis can be used to determine the specificity and/or the sensitivity of a given diagnosis based upon subjecting a patient to the decision tree described herein in order to predict an outcome for a pediatric patient with septic shock.

The correlations disclosed herein, between pediatric patient septic shock biomarker levels and/or mRNA levels and/or gene expression levels, provide a basis for conducting a diagnosis of septic shock, or for conducting a stratification of patients with septic shock, or for enhancing the reliability of a diagnosis of septic shock by combining the results of a quantification of a septic shock biomarker with results from other tests or indicia of septic shock. For example, the results of a quantification of one biomarker could be combined with the results of a quantification of one or more additional biomarker, cytokine, mRNA, or the like. Thus, even in situations in which a given biomarker correlates only moderately or weakly with septic shock, providing only a relatively small PPV, NPV, specificity, and/or sensitivity, the correlation can be one indicium, combinable with one or more others that, in combination, provide an enhanced clarity and certainty of diagnosis. Accordingly, the methods and materials of the invention are expressly contemplated to be used both alone and in combination with other tests and indicia, whether quantitative or qualitative in nature.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

The original pediatric sepsis risk model, PERSEVERE, uses biomarkers to estimate baseline mortality risk for pediatric septic shock. Prior to the work described here, it was unknown how PERSEVERE performs within distinct septic shock phenotypes. We therefore tested PERSEVERE in children with septic shock and thrombocytopenia-associated multiple organ failure (TAMOF), and in those without new onset thrombocytopenia but with multiple organ failure (MOF). Design: PERSEVERE-based mortality risk was generated for each study subject (n=660). A priori, we determined that if PERSEVERE did not perform well in both the TAMOF and MOF cohorts, we would revise PERSEVERE to incorporate admission platelet counts. The revised model is referred to as PERSEVERE-II.

Results

PERSEVERE Performance in Subjects with TAMOF and MOF

Table 1 shows the demographics and clinical characteristics of the TAMOF, MOF and No MOF cohorts. Subjects with TAMOF (n=209) had a higher mortality, a higher rate of complicated course, and a higher median PRISM score when compared to the MOF (n=290) and No MOF (n=161) subjects. A lower proportion of subjects with TAMOF had no causative pathogen isolated, and a lower proportion had comorbidities when compared to the MOF and No MOF subjects. The subjects with No MOF were older than the TAMOF and MOF subjects. No other differences were noted.

Table 2 shows the test characteristics of PERSEVERE for estimating the probability of 28-day mortality in all subjects and for subjects in the TAMOF, MOF, and no MOF groups. PERSEVERE had very good performance in the TAMOF cohort, with an AUC of 0.84 (95% CI: 0.77-0.90), a sensitivity of 91% (95% CI: 79-97), and a negative likelihood ratio of 0.1 (95% CI: 0.01-0.3). In contrast, PERSEVERE performed less well in the MOF group, with an AUC of just 0.71 (0.61-0.80).

Derivation of PERSEVERE-II

Because PERSEVERE did not perform equally well in the TAMOF group and the MOF group, we proceeded to revise PERSEVERE taking into account variables associated with thrombocytopenia. FIG. 1 shows PERSEVERE-II. The top node of the decision tree, the root node, provides the total number of subjects as well as the number and proportion of survivors and nonsurvivors. Subjects in the root node are subsequently allocated to daughter nodes based on the results of binary recursive partitioning. Each daughter node provides the criterion for deciding subsequent partitions, along with the number and proportion of survivors and nonsurvivors. Terminal nodes reflect the final assignment of risk to an individual case. We have annotated the tree to number the terminal nodes; the numbers appear in bold above each terminal node in the tree. All five PERSEVERE biomarkers (CCL3, IL8, GZMB, HSPA1B, and MMP8) contributed to the predictive capacity of PERSEVERE-II. Admission platelet count was found to augment predictive accuracy, but age and comorbidity burden did not.

PERSEVERE-II had five low risk terminal nodes (<1.9% risk of death; nodes 1, 2, 5, 8, and 9), four intermediate risk terminal nodes (16.7% to 33.3% risk of death; nodes 4, 6, 7, and 10), and two high risk terminal nodes (>44.4% risk of death; nodes 3 and 11). Among the 273 subjects classified as low risk, two (0.7%) died by 28 days. Among the 151 subjects classified as intermediate or high risk, 47 (31.1%) died by 28 days. Table 3 shows the test characteristics of PERSEVERE-II in the derivation cohort.

TABLE 1

Demographics and clinical characteristics of the study cohorts.

|  | TAMOF | MOF | No MOF |
| --- | --- | --- | --- |
| N (%) | 209 (32) | 290 (44) | 161 (24) |
| Median Age, Years (IQR) | 2.1 (0.7-6.5) | 3.0 (1.0-7.1) | 7.0 (2.6-13.0)[1] |
| Males, # (%) | 122 (58) | 158 (54) | 83 (52) |
| 28-day mortality, # (%) | 47 (22)[2] | 39 (13)[3] | 0 (0) |
| Complicated course, # (%) | 99 (47)[2] | 87 (30)[3] | 0 (0) |
| Median PRISM score (IQR) | 17 (11-24)[2] | 11 (7-17)[3] | 9 (5-12) |
| # with gram negative bacteria (%) | 60 (29) | 61 (21) | 32 (20) |
| # with gram positive bacteria (%) | 57 (27) | 56 (19) | 29 (18) |
| # with other pathogen isolated (%) | 18 (9) | 25 (9) | 13 (8) |
| # with no pathogen identified (%) | 74 (35)[2] | 148 (51) | 87 (54) |
| # with comorbidity (%) | 79 (38)[3] | 148 (51) | 76 (47) |
| # with malignancy (%) | 0 (0)[2] | 53 (18) | 28 (17) |
| # with immune suppression (%) | 12 (6)[2] | 67 (23) | 34 (21) |
| # with bone marrow transplantation (%) | 0 (0)[2] | 25 (9) | 13 (8) |

[1] p < 0.05 vs. TAMOF and MOF.
[2] p < 0.05 vs. MOF and No MOF.
[3] p < 0.05 vs. MOF.

TABLE 2

PERSEVERE test characteristics across the study cohorts.

|  | ALL SUBJECTS | TAMOF | MOF | NO MOF |
| --- | --- | --- | --- | --- |
| N | 660 | 209 | 290 | 161 |
| False Positive | 151 | 57 | 77 | 17 |
| True Positive | 72 | 43 | 29 | 0 |
| True Negative | 424 | 105 | 175 | 144 |
| False Negative | 13 | 4 | 9 | 0 |
| Sensitivity | 85 (75-91) | 91 (79-97) | 76 (59-88) | — |
| Specificity | 74 (70-77) | 65 (57-72) | 69 (58-69) | — |
| PPV | 32 (26-39) | 43 (33-53) | 27 (19-37) | — |
| NPV | 97 (95-98) | 96 (90-99) | 95 (91-98) | — |
| +LR | 3.2 (2.7-3.8) | 2.6 (2.1-3.3) | 2.5 (1.9-3.2) | — |
| −LR | 0.2 (0.1-0.3) | 0.1 (0.05-0.3) | 0.3 (0.2-0.6) | — |
| AUC | 0.80 (0.75-0.86) | 0.84 (0.77-0.90) | 0.71 (0.61-0.80) | — |

TABLE 3

PERSEVERE-II test characteristics in the derivation and test cohorts.

| | ALL SUBJECTS | TAMOF | MOF | NO MOF |
|---|---|---|---|---|
| Derivation cohort, N = 424 | | | | |
| N | 424 | 159 | 155 | 110 |
| False Positive | 104 | 57 | 26 | 21 |
| True Positive | 47 | 34 | 13 | — |
| True Negative | 271 | 66 | 116 | 89 |
| False Negative | 2 | 2 | 0 | — |
| Sensitivity | 96 (85-99) | 94 (80-99) | 100 (72-100) | — |
| Specificity | 72 (67-77) | 54 (44-63) | 82 (74-87) | — |
| PPV | 36 (31-40) | 37 (28-48) | 33 (20-50) | — |
| NPV | 99 (97-100) | 97 (89-99) | 100 (96-100) | — |
| +LR | 3.5 (2.9-4.1) | 2.0 (1.7-2.5) | 5.5 (3.9-7.7) | — |
| −LR | 0.06 (0.01-0.2) | 0.1 (0.03-0.4) | — | — |
| AUC | 0.89 (0.85-0.93) | 0.82 (0.75-0.88) | 0.93 (0.88-0.97) | — |
| Test cohort, N = 236 | | | | |
| N | 236 | 50 | 135 | 51 |
| False Positive | 61 | 17 | 36 | 8 |
| True Positive | 34 | 11 | 23 | — |
| True Negative | 138 | 22 | 73 | 43 |
| False Negative | 3 | 0 | 3 | — |
| Sensitivity | 92 (77-98) | 100 (68-100) | 88 (69-97) | — |
| Specificity | 69 (62-76) | 56 (40-72) | 67 (57-76) | — |
| PPV | 36 (26-46) | 39 (22-59) | 39 (27-53) | — |
| NPV | 98 (93-99) | 100 (82-100) | 96 (88-99) | — |
| +LR | 3.0 (2.4-3.8) | 2.3 (1.6-3.3) | 2.7 (2.0-3.6) | — |
| −LR | 0.1 (0.04-0.3) | — | 0.2 (0.1-0.5) | — |
| AUC | 0.84 (0.78-0.90) | 0.92 (0.84-1.00) | 0.79 (0.71-0.88) | — |

Testing PERSEVERE-II

Figure 2:
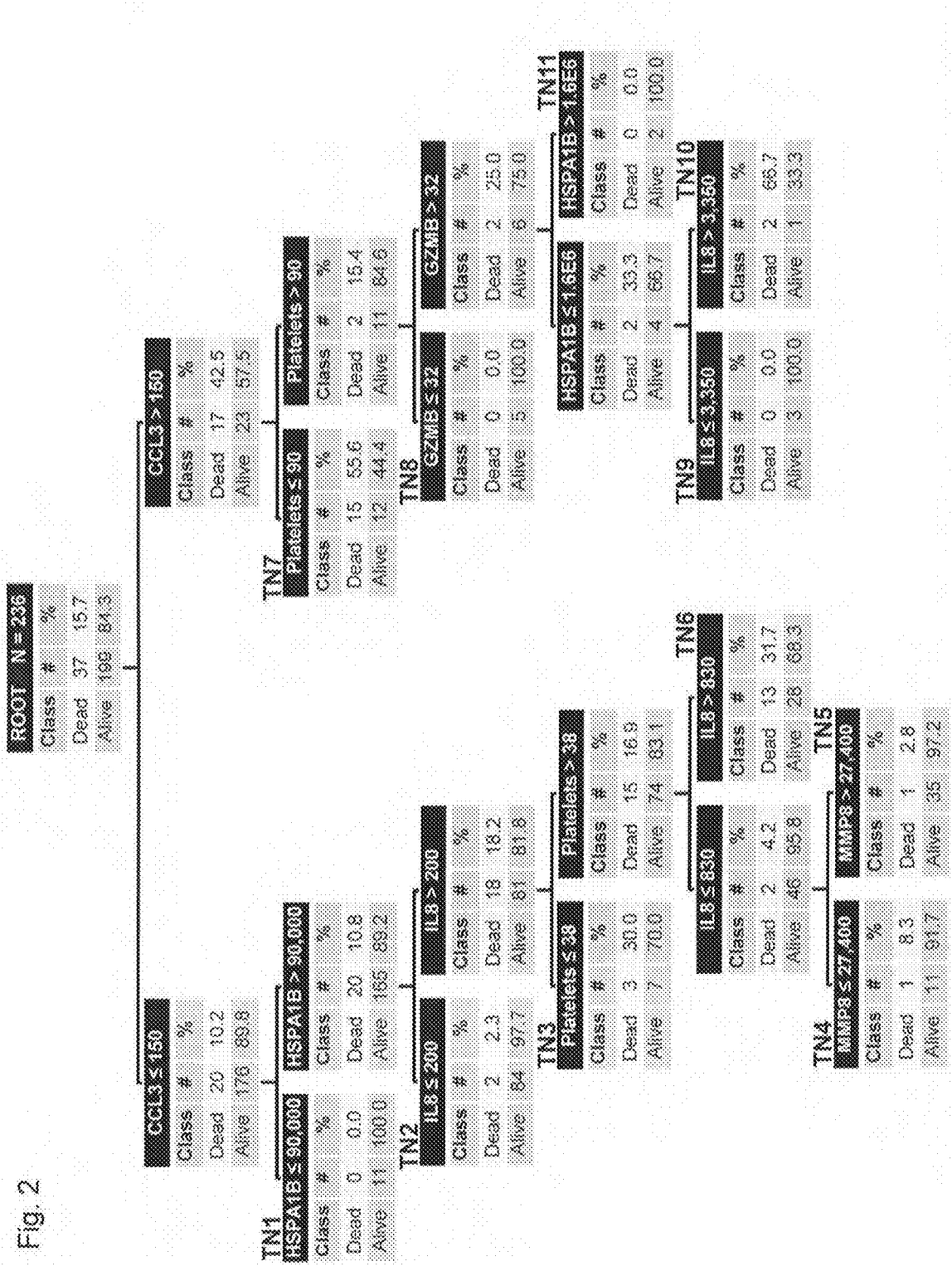
FIG. 2 shows how 236 additional subjects were classified.

We tested the performance of PERSEVERE-II using the 236 subjects newly enrolled since the initial derivation of PERSEVERE. FIG. 2 shows how the 236 test subjects were classified. Among the 141 test subjects classified as low risk, three (2.1%) died by 28 days. Among the 95 test subjects classified as intermediate or high risk, 34 (35.8%) died by 28 days. Table 3 shows the test characteristics of PERSEVERE-II in the test cohort.

Comparison of PERSEVERE and PERSEVERE-II

Figure 3:
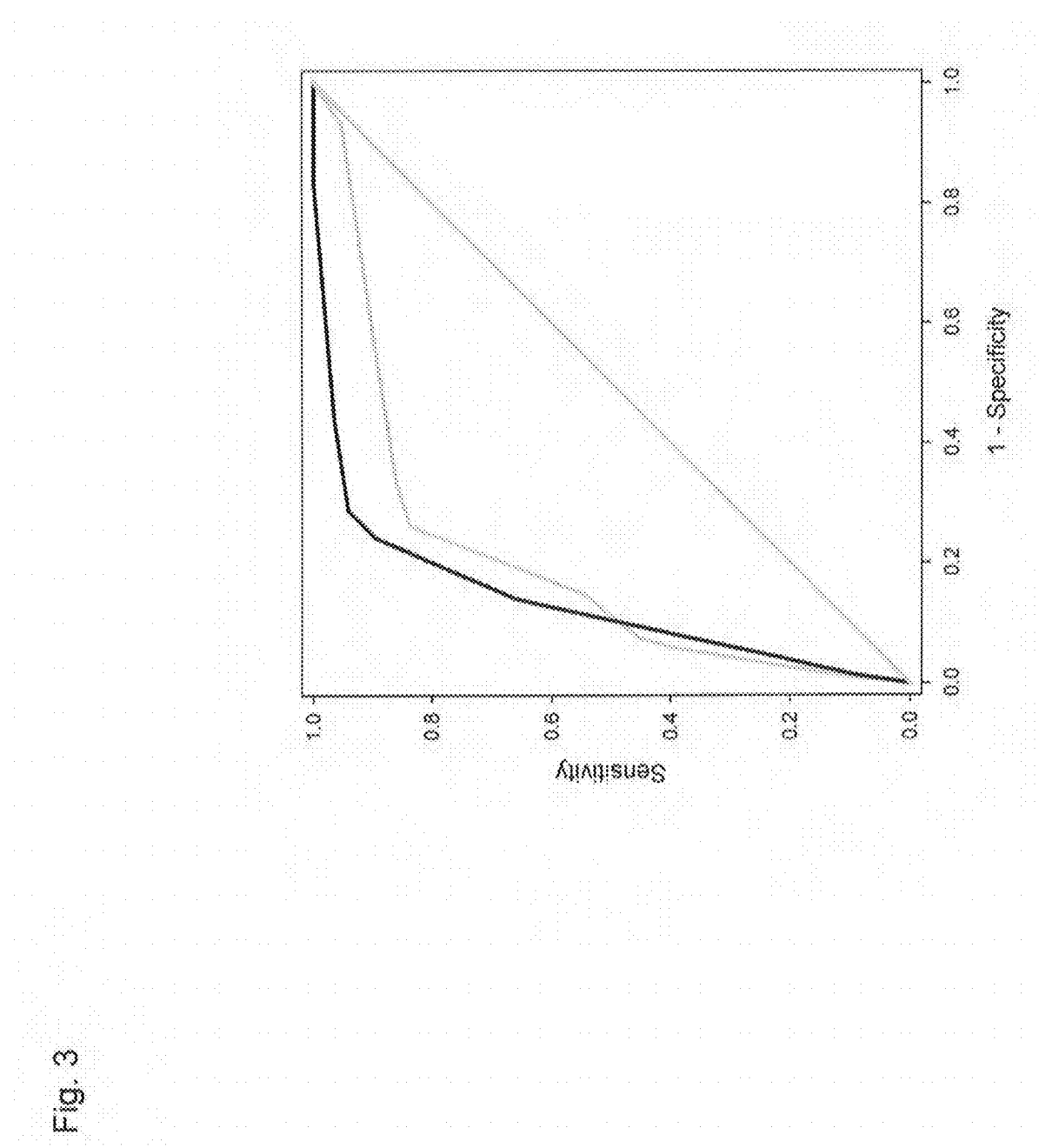
FIG. 3 shows the PERSEVERE and PERSEVERE-II receiver operating characteristic curves for all subjects.

FIG. 3 shows the PERSEVERE and PERSEVERE-II receiver operating characteristic curves for all subjects. For estimating the risk of 28-day mortality, the AUC for PERSEVERE-II (0.87; 95% CI 0.84-0.90) was superior to that of PERSEVERE (0.80; 95% CI 0.75-0.86; p=0.031). When risk stratifying using PERSEVERE-II compared to PERSEVERE, the NRI was 0.50 (95% CI: 0.28-0.72; p<0.0001), indicating improved classification of subjects. Admission platelet count alone had an AUC of 0.73 (95% C.I. 0.68-0.78) for estimating the risk of 28-day mortality.

Designing a Clinical Trial to Test the Efficacy of Plasma Exchange Using PERSEVERE-II as a Prognostic Enrichment Strategy One practical application of PERSEVERE is as a prognostic enrichment tool to inform patient selection for clinical trials. For example, PERSEVERE-II could allow for exclusion of patients having a low baseline mortality probability with standard care and who would unlikely benefit from an experimental intervention. Exclusion of such patients could enrich the study population with patients having a higher baseline mortality probability, and consequently decrease the number of patients required for an interventional trial. As an example, one recent trial used the approach of restricting enrollment to patients with three or more organ failures as a means of enriching the study population with more severely ill patients (clinicaltrials.gov; NCT00118664).

In our study, 108 of the TAMOF subjects had at least three organ failures and could therefore have theoretically met the enrollment criteria for NCT00118664. We used data from these 108 subjects enrolled in our study to estimate the sample size required to conduct a clinical trial testing the efficacy of plasma exchange in children with TAMOF, with and without PERSEVERE-based stratification.

Among these 108 subjects there were 41 deaths (38% mortality), and PERSEVERE-II had an AUC of 0.82 (95% CI: 0.74-0.90) for estimating 28-day mortality. In comparison, PRISM had an AUC of 0.60 (95% CI: 0.49-0.72) for estimating 28-day mortality in these subjects. PERSEVERE-II correctly predicted 28-day survival for 32 subjects (true negatives) and incorrectly predicted 28-day survival for 2 subjects (false negatives). Using PERSEVERE-II-based stratification, these true and false negative subjects would be excluded from a clinical trial, leaving 39 true positive and 35 false positive subjects for inclusion. Among the true and false positive subjects, the 28-day mortality was 53%.

We calculated the number of un-stratified patients (38% mortality) and PERSEVERE-II-stratified patients (53% mortality) required in a trial randomizing patients with TAMOF and at least 3 organ failures to standard care or plasma exchange. We used a range of assumptions for the relative mortality reduction attributable to plasma exchange (10% to 50%), and we set power (1-β) to 0.8 and α to 0.05. Table 4 shows the results. In each scenario, PERSEVERE- II-based stratification reduced the number of subjects needed in each study arm by between 39% and 44%.

TABLE 4

Number of un-stratified and PERSEVERE-II-based stratified subjects required in each study arm in a trial of plasma exchange for TAMOF (assuming a continuity corrected chi-square test to compare two equally sized groups with power (1-β) set to 0.8 and α = 0.05).

| Projected relative reduction in mortality with plasma exchange | No. of un-stratified patients required in each study arm (% absolute mortality reduction) | No. of stratified patients required in each study arm (% absolute mortality reduction) |
|---|---|---|
| 10% | 2,559 (3.8) | 1,434 (5.3) |
| 20% | 637 (7.6) | 366 (10.6) |
| 30% | 281 (11.4) | 165 (15.9) |
| 40% | 156 (15.2) | 94 (21.2) |
| 50% | 98 (19.0) | 60 (26.5) |

Discussion

Given the clinical and research interest in TAMOF as a distinct clinical phenotype of septic shock, we tested the performance of PERSEVERE in children with septic shock and TAMOF and found it had acceptable performance. In contrast, PERSEVERE did not perform well in children with septic shock and MOF in the absence of new onset thrombocytopenia. We revised PERSEVERE to have broader applicability across septic shock phenotypes. PERSEVERE-II incorporates admission platelet count into the risk stratification, and performs well in both the TAMOF and MOF phenotypes. This feature of PERSEVERE-II is biologically plausible because new onset thrombocytopenia is the primary determinant when distinguishing TAMOF from MOF [11, 12]. PERSEVERE-II continued to perform well when tested in a separate cohort. Our data demonstrate that PERSEVERE-II outperforms PERSEVERE, as measured by comparisons of the receiver operating characteristic curves and the NRI.

The current study supports the concept that TAMOF is a distinct clinical phenotype of septic shock [Nguyen et al. Thrombocytopenia-associated multiple organ failure. In: Pediatric Critical Care Medicine: Basic Science and Clinical Practice. Edited by Wheeler D S, Wong H R, Shanley T P, vol. 3. New York: Springer; 2014: 481-492]. Patients with septic shock and TAMOF had significantly higher rates of mortality and complicated course compared to patients with MOF in the absence of new onset thrombocytopenia. Thus, the design of therapies specifically targeting the TAMOF phenotype seems warranted.

Plasma exchange may be a potential therapy for TAMOF, but it has not been tested in a randomized clinical trial. The American Society of Apheresis classifies the use of plasma exchange for "sepsis with multiple organ failure" as being supported with only level III evidence, and they provide a grade 2B recommendation [Schwartz J, et al. Guidelines on the use of therapeutic apheresis in clinical practice-evidence-based approach from the Writing Committee of the American Society for Apheresis: the sixth special issue. J Clin Apher 2013, 28(3):145-284]. This states that the role of plasma exchange in this condition is not truly established, and that the supporting evidence is considered weak and of moderate quality. Because plasma exchange carries more than minimal risk given the need for large caliber central venous access, exposure to blood products, and need for an extracorporeal circuit, a rational strategy for using plasma exchange as a therapeutic strategy for TAMOF should optimize the risk to benefit ratio.

A potential strategy for optimizing the risk to benefit ratio when employing higher risk experimental therapies is to stratify patients based on baseline mortality risk. This concept is known as prognostic enrichment [Temple R: Enrichment of clinical study populations. Clin Pharmacol Ther 2010, 88(6):774-778]. By using a tool to estimate outcome risk, prognostic enrichment selects patients with a greater event rate. Because sample size for an event-based study is inversely proportional to effect size and directly proportional to event rate, prognostic enrichment can allow for a smaller sample size Importantly, prognostic enrichment does not affect relative risk reduction, but will increase the absolute effect size of an experimental therapy.

A recent publication opined that severity scores such as Acute Physiology and Chronic Health Evaluation (APACHE) and PRISM should not be used as entry criteria for clinical trials and provided several reasons in support [Vincent J L, Opal S M, Marshall J C: Ten reasons why we should NOT use severity scores as entry criteria for clinical trials or in our treatment decisions. Crit Care Med 2010, 38(1):283-287]. The publication further called for the development of biomarker-based stratification strategies as a means to enhance selection criteria for clinical trials. The utility of PERSEVERE as an enrichment strategy is consistent with this recommendation.

We tested the concept of prognostic enrichment in the design of a trial of plasma exchange for patients meeting TAMOF criteria, based on entry criteria from a recent observational study. We demonstrate that when eligible patients are stratified for baseline mortality risk using PERESEVERE-II, the sample size needed to demonstrate efficacy is substantially reduced when compared to no stratification. The simulation demonstrates how almost one third of patients with septic shock and TAMOF could theoretically be spared exposure to plasma exchange based on a reliable estimation of low baseline mortality risk with standard care.

We note three main limitations of our study. First, in the absence of pre-PICU admission platelet count data we considered thrombocytopenia to be of new onset when the study subject had an admission platelet count <100,000/μl and did not have a comorbidity associated with thrombocytopenia. Conversely, in subjects with a comorbidity associated with thrombocytopenia, any thrombocytopenia event was considered related to the comorbidity, rather than being of new onset. This could have led to misclassification of some subjects. Second, the test cohort used for internal validation was a convenience sample representing subjects newly enrolled since the derivation and validation of PERSEVERE. We are in the process of enrolling a prospective cohort in which to validate the performance of PERSEVERE-II. Finally, because PERSEVERE is designed to assign a baseline mortality probability, we only considered admission platelet counts in the modeling process. This precludes analysis of how temporal changes in platelet counts are associated with changing risk. We have developed a temporal version of PERSEVERE and will pursue the opportunity to consider how changes in platelet counts reflect changing risk over time.

In conclusion, testing the accuracy of PERSEVERE in the context of organ failure phenotypes of septic shock prompted a revision of PERSEVERE incorporating admission platelet count information. PERSEVERE-II performs well upon testing, independent of TAMOF or MOF status. Tools such as PERSEVERE-II have the potential to provide prognostic enrichment for a trial of plasma exchange in children with septic shock and TAMOF.

Methods

Study Subjects and Data Collection: The study cohort included 660 subjects with septic shock. There were 424 subjects with available platelet data previously reported in the derivation and validation of PERSEVERE [Wong H R, et al: The pediatric sepsis biomarker risk model. Crit Care 2012, 16(5):R174; Wong H R, et al: Testing the prognostic accuracy of the updated pediatric sepsis biomarker risk model. PLoS One 2014, 9(1):e86242]. An additional 236 new subjects newly enrolled since the derivation and validation of PERSEVERE were also included. No subjects received plasma exchange for TAMOF.

The protocol for collection and use of biological specimens and clinical data was approved by the Institutional Review Boards of each of the 18 participating institutions. Children≤18 years of age admitted to the pediatric intensive care unit (PICU) and meeting pediatric-specific consensus criteria for septic shock were eligible for enrollment [Goldstein B, Giroir B, Randolph A: International pediatric sepsis consensus conference: definitions for sepsis and organ dysfunction in pediatrics. Pediatr Crit Care Med 2005, 6(1):2-8; Wong H R, et al: Genome-level expression profiles in pediatric septic shock indicate a role for altered zinc homeostasis in poor outcome. Physiol Genomics 2007, 30(2):146-155]. There were no exclusion criteria, other than the inability to obtain informed consent, which was obtained from parents or legal guardians prior to any data or sample collection.

Serum samples were obtained within 24 hours of first meeting the criteria for septic shock in the PICU, which was typically at presentation to the PICU. Clinical and laboratory data were collected daily while in the PICU. Organ failure data were tracked up to day 7 of septic shock using previously published criteria [Goldstein B, Giroir B, Randolph A: International pediatric sepsis consensus conference: definitions for sepsis and organ dysfunction in pediatrics. Pediatr Crit Care Med 2005, 6(1):2-8]. Mortality was tracked for 28 days after enrollment. Complicated course was defined as the persistence of two or more organ failures at day seven of septic shock or 28-day mortality [Wong H R, et al: Developing a clinically feasible personalized medicine approach to pediatric septic shock. Am J Respir Crit Care Med 2015, 191(3):309-315]. Illness severity was estimated using PRISM scores [Pollack M M, Patel K M, Ruttimann U E: The Pediatric Risk of Mortality III—Acute Physiology Score (PRISM III-APS): a method of assessing physiologic instability for pediatric intensive care unit patients. J Pediatr 1997, 131(4):575-581].

Definition of TAMOF and MOF: TAMOF was defined as new onset thrombocytopenia (platelet count<100,000/µL) and two or more organ failures [Nguyen TC et al.: Thrombocytopenia-associated multiple organ failure. In: Pediatric Critical Care Medicine: Basic Science and Clinical Practice. Edited by Wheeler D S, Wong H R, Shanley T P, vol. 3. New York: Springer; 2014: 481-492; Nguyen T C, et al.: Acquired ADAMTS-13 deficiency in pediatric patients with severe sepsis. Haematologica 2007, 92(1):121-124]. MOF was defined as new onset of two or more organ failures but with either platelet counts ≥100,000/µL or with a known pre-existing condition resulting in thrombocytopenia. All other subjects were classified in the No MOF group.

PERSEVERE Biomarkers: PERSEVERE includes C-C chemokine ligand 3 (CCL3), interleukin 8 (IL8), heat shock protein 70 kDa 1B (HSPA1B), granzyme B (GZMB), and matrix metallopeptidase 8 (MMP8) [Wong H R, et al: The pediatric sepsis biomarker risk model. Crit Care 2012, 16(5):R174]. Serum concentrations of these biomarkers were measured using a multi-plex magnetic bead platform (MILLIPLEX™ MAP) designed for this project by the EMD Millipore Corporation (Billerica, Mass.). Biomarker concentrations were measured in a Luminex® 100/200 System (Luminex Corporation, Austin, Tex.), according the manufacturers' specifications. Assay performance data were previously published [Wong H R, et al: The pediatric sepsis biomarker risk model. Crit Care 2012, 16(5):R174].

Statistical Analysis: Initially, data are described using medians, interquartile ranges, frequencies, and percentages. Comparisons between groups used the Mann-Whitney U-test, Chi-square, or Fisher's Exact tests as appropriate. Descriptive statistics and comparisons used SigmaStat Software (Systat Software, Inc., San Jose, Calif.).

Each study subject was assigned a 28 day mortality probability using the previously published PERSEVERE model [Wong H R, et al: The pediatric sepsis biomarker risk model. Crit Care 2012, 16(5):R174]. PERSEVERE performance is reported using diagnostic test statistics with 95% confidence intervals computed using the score method as implemented by the VassarStats Website for Statistical Computation.

A priori, we determined that if PERSEVERE did not fit equally well in patients with TAMOF as in patients without TAMOF, we would revise PERSEVERE to incorporate variables associated with thrombocytopenia. Specifically, we considered the presence of malignancy, immune suppression, bone marrow transplantation, and new onset thrombocytopenia as dichotomous predictor variables. Continuous predictor variables included the PERSEVERE biomarkers, age, and admission platelet count. To revise PERSEVERE, we used CART methodology (Salford Predictive Modeler v6.6, Salford Systems, San Diego, Calif.) [Che D, et al: Decision tree and ensemble learning algorithms with their applications in bioinformatics. Adv Exp Med Biol 2011, 696:191-199; Muller R, Mockel M: Logistic regression and CART in the analysis of multimarker studies. Clin Chim Acta 2008, 394(1-2):1-6]. The primary outcome variable was 28-day mortality. Weighting of cases and the addition of cost for misclassification were not used in the modeling procedures. The code and data used to generate the model is available from the authors. The revised tree (PERSEVERE-II) was derived using the original 424 subjects used to develop PERSEVERE, and was subsequently internally validated in the 236 newly enrolled subjects.

Areas under the receiver operating characteristic curves (AUC) were compared using the method of Hanley and McNeil for non-independent samples [Hanley J A, McNeil B J: A method of comparing the areas under receiver operating characteristic curves derived from the same cases. Radiology 1983, 148(3):839-843]. The net reclassification improvement (NRI) was used to estimate the incremental predictive ability of PERSEVERE-II compared to PERSEVERE [Steyerberg E W, Vickers A J, Cook N R, Gerds T, Gonen M, Obuchowski N, Pencina M J, Kattan M W: Assessing the performance of prediction models: a framework for traditional and novel measures. Epidemiology 2010, 21(1):128-138]. The NRI was computed using the R-package Hmisc.

Finally, we estimated the sample size needed for conducting a clinical trial comparing plasma exchange to no plasma exchange in children with TAMOF. We considered using PERSEVERE-II as an enrichment strategy to target patients most likely to benefit from plasma exchange. We assumed independence of study arms would be tested using a continuity corrected Chi-square test with power (1-β) set to 0.8 and α=0.05. Calculations were conducted using nQuery Advisor v 7.0 (Statistical Solutions Ltd., Cork, Ireland).

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method of treating septic shock in a pediatric patient presenting with multiple organ failure (MOF) in the absence of new onset thrombocytopenia, the method comprising obtaining at least one biological sample from the patient presenting with multiple organ failure (MOF) in the absence of new onset thrombocytopenia;

determining a blood platelet count and the amount of each of the following protein biomarkers in the at least one biological sample: C-C chemokine ligand 3 (CCL3), heat shock protein 70 kDa 1B (HSPA1B), interleukin-8 (IL8), granzyme B (GZMB), and matrix metalloproteinase 8 (MMP8);

classifying the patient as intermediate or high risk of mortality based on the blood platelet count and the amount of each of the protein biomarkers in the sample; and treating the intermediate or high risk patient with a treatment selected from the group consisting of extracorporeal membrane oxygenation/life support, plasmapheresis, plasma exchange, pulmonary artery catheterization, high volume continuous hemofiltration, and combinations thereof.

2. A method of classifying risk of mortality and treating a pediatric patient with septic shock presenting with multiple organ failure (MOF) in the absence of new onset thrombocytopenia the method comprising:

obtaining a biological sample from the patient;

determining a blood platelet count and the amount of each of the following protein biomarkers in the at least one biological sample: platelets, C-C chemokine ligand 3 (CCL3), heat shock protein 70 kDa 1B (HSPA1B), interleukin-8 (IL8), granzyme B (GZMB), and matrix metalloproteinase 8 (MMP8); and classifying the patient as intermediate risk if any of the following are true:

a) an amount of CCL3 protein less than or equal to 150 pg/ml, an amount of HSPA1B greater than 90,000 pg/ml, an amount of IL8 protein greater than 200 pg/ml, a platelet count greater than 38/mm$^3$, an amount of IL8 protein less than or equal to 830 pg/ml, and an amount of MMP8 protein less than or equal to 27,400 pg/ml, or b) an amount of CCL3 protein less than or equal to 150 pg/ml, a amount of HSPA1B protein greater than 90,000 pg/ml, an amount of IL8 protein greater than 200 pg/ml, a platelet count greater than 38/mm$^3$, and an amount of IL8 protein greater than 830 pg/ml, or c) an amount of CCL3 protein greater than 150 pg/ml, and a platelet count less than or equal to 90/mm$^3$, or d) an amount of CCL3 protein greater than 150 pg/ml, a platelet count greater than 90/mm$^3$, an amount of GZMB protein greater than 32 pg/ml, an amount of HSPA1B protein less than or equal to 1.6×10$^6$ pg/ml, and an amount of IL8protein greater than 3,350 pg/ml; and classifying the patient as high risk if any of the following are true:

e) an amount of CCL3 protein less than or equal to 150 pg/ml, an amount of HSPA1B protein greater than 90,000 pg/ml, an amount of IL8 protein greater than 200 pg/ml, and a platelet count less than or equal to 38/mm$^3$, or f) an amount of CCL3 protein greater than 150 pg/ml, a platelet count greater than 90/mm$^3$, an amount of GZMB protein greater than 32 pg/ml, and an amount of HSPA1B protein greater than 1.6×10$^6$ pg/ml; and treating the intermediate or high risk patient with a treatment selected from the group consisting of extracorporeal membrane oxygenation/life support, plasmapheresis, plasma exchange, pulmonary artery catheterization, high volume continuous hemofiltration, and combinations thereof.

3. The method of claim 1, wherein the classifying is performed using a classification and regression tree methodology.

4. The method of claim 1, wherein the sample is obtained within the first hour of presentation with septic shock.

5. The method of claim 1, wherein the sample is obtained within the first 48 hours of presentation with septic shock.

6. The method of claim 1, wherein the protein biomarkers are blood proteins and the biological sample is whole blood or plasma, or a combination thereof.

* * * * *

UNITED STATES PATENT AND TRADEMARK OFFICE
CERTIFICATE OF CORRECTION

PATENT NO. : 10,261,068 B2
APPLICATION NO. : 15/171418
DATED : April 16, 2019
INVENTOR(S) : Wong et al.

Page 1 of 1

It is certified that error appears in the above-identified patent and that said Letters Patent is hereby corrected as shown below:

On the Title Page

Item (12) "Wong" should read -- Wong, et al. --.

Item (72) Inventor is corrected to read:
-- Hector R. Wong, Cincinnati (OH);
Christopher J. Lindsell, Cincinnati (OH) --.

Signed and Sealed this
Fifteenth Day of October, 2019

Andrei Iancu
*Director of the United States Patent and Trademark Office*